(12) United States Patent
Kubota et al.

(10) Patent No.: US 6,274,754 B1
(45) Date of Patent: Aug. 14, 2001

(54) PREPARATION OF BIS(3-AMINOPROPYLDIMETHYLSILYL)BENZENE COMPOUNDS

(75) Inventors: Tohru Kubota; Mikio Endo; Yasufumi Kubota, all of Niigata-Ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/307,768

(22) Filed: May 10, 1999

(30) Foreign Application Priority Data

May 11, 1998 (JP) .................................................. 10-145079

(51) Int. Cl.⁷ ..................................................... C07F 7/10
(52) U.S. Cl. ............................................................. 556/413
(58) Field of Search ............................................. 556/413

(56) References Cited

U.S. PATENT DOCUMENTS 4,927,953 * 5/1990 Takatsuna et al. .................... 556/413
5,047,526 * 9/1991 Yamamoto ............................ 540/200
5,227,504 * 7/1993 Shinohara et al. .................... 556/411

OTHER PUBLICATIONS

Izv. Akad Nauk SSSR Ser. Khim., 2449 (1969).

Dokl. Akad Nauk SSSR, 179, 600 (1968).

* cited by examiner

*Primary Examiner*—Paul F. Shaver
(74) *Attorney, Agent, or Firm*—Millen, White, Zelano & Branigan, P.C.

(57) ABSTRACT

1,2-, 1,3- or 1,4-bis(3-aminopropyldimethylsilyl)benzene is prepared by effecting hydrosilylation reaction between N,N-bis(trimethylsilyl)allylamine and 1,2-, 1,3- or 1,4-bis (dimethylsilyl)benzene in the presence of a platinum catalyst, followed by detrimethylsilylation reaction. The process is simple and inexpensive to synthesize the end compound in high yields without forming isomers.

1 Claim, 4 Drawing Sheets

PREPARATION OF BIS(3-AMINOPROPYLDIMETHYLSILYL)BENZENE COMPOUNDS

This invention relates to a novel process for preparing bis(3-aminopropyldimethylsilyl)benzene compounds which are useful as a modifier for polyimides for use in semiconductor isolation films and liquid crystal alignment layers or a modifier for polyamides, polyurethane, etc.

BACKGROUND OF THE INVENTION

Bis(3-aminopropyldimethylsilyl)benzene compounds are useful as a modifier for polyimides for use in semiconductor isolation films, semiconductor manufacturing photosensitive resins, and liquid crystal alignment layers for improving adhesion and moldability thereof or a modifier for polyamides, polyurethane, etc. for tailoring properties thereof.

Several processes are known for preparing bis(3-aminopropyldimethylsilyl)benzene compounds. One known process for producing 1,4-bis(3-aminopropyldimethylsilyl)benzene is by effecting direct hydrosilylation reaction between allylamine and 1,4-bis(dimethylsilyl)benzene in the presence of a platinum catalyst (Izv. Akad. Nauk SSSR Ser. Khim., 2249 (1969)). Another process is effecting hydrosilylation reaction between N-(trimethylsilyl)-allylamine and 1,4-bis(dimethylsilyl)benzene in the presence of a platinum catalyst, followed by detrimethylsilylation reaction (Dokl. Akad. Nauk SSSR, 179, 600 (1968)).

However, the former process is low in yields and difficult to produce the end compound of high purity because the reaction is not only very slow and time consuming, but also entails many side reactions. The latter process has the drawback that the starting reactant, N-(trimethylsilyl) allylamine is difficult to handle because it is so reactive that it is likely to decompose with humidity in air. There is available no commercial process for preparing N-(trimethylsilyl)-allylamine.

In addition, either of these processes has the problem that hydrosilylation reaction entails large amounts of isomers in which addition takes place internally rather than at terminals, resulting in the end compound having admixed therein (2-aminopropyldimethylsilyl)(3-aminopropyldimethylsilyl)benzene. This isomer is heat unstable as compared with the end compound. When the product having the isomer admixed therein is used in the polyimide-modifying application where heat resistance is important, the performance of the product is unsatisfactory.

SUMMARY OF THE INVENTION

Therefore, an object of the invention is to provide a novel and improved process for preparing a bis(3-aminopropyldimethylsilyl)benzene compound in a simple and inexpensive manner and in high yields without forming isomers.

We have found that by effecting hydrosilylation reaction between N,N-bis(trimethylsilyl)allylamine and a bis(dimethylsilyl)benzene compound in the presence of a platinum catalyst, then effecting detrimethylsilylation reaction, a bis(3-aminopropyldimethylsilyl)benzene compound can be synthesized in high yields without forming isomers. The process is simple and inexpensive to synthesize the end compound.

DETAILED DESCRIPTION OF THE INVENTION

Figure 1:
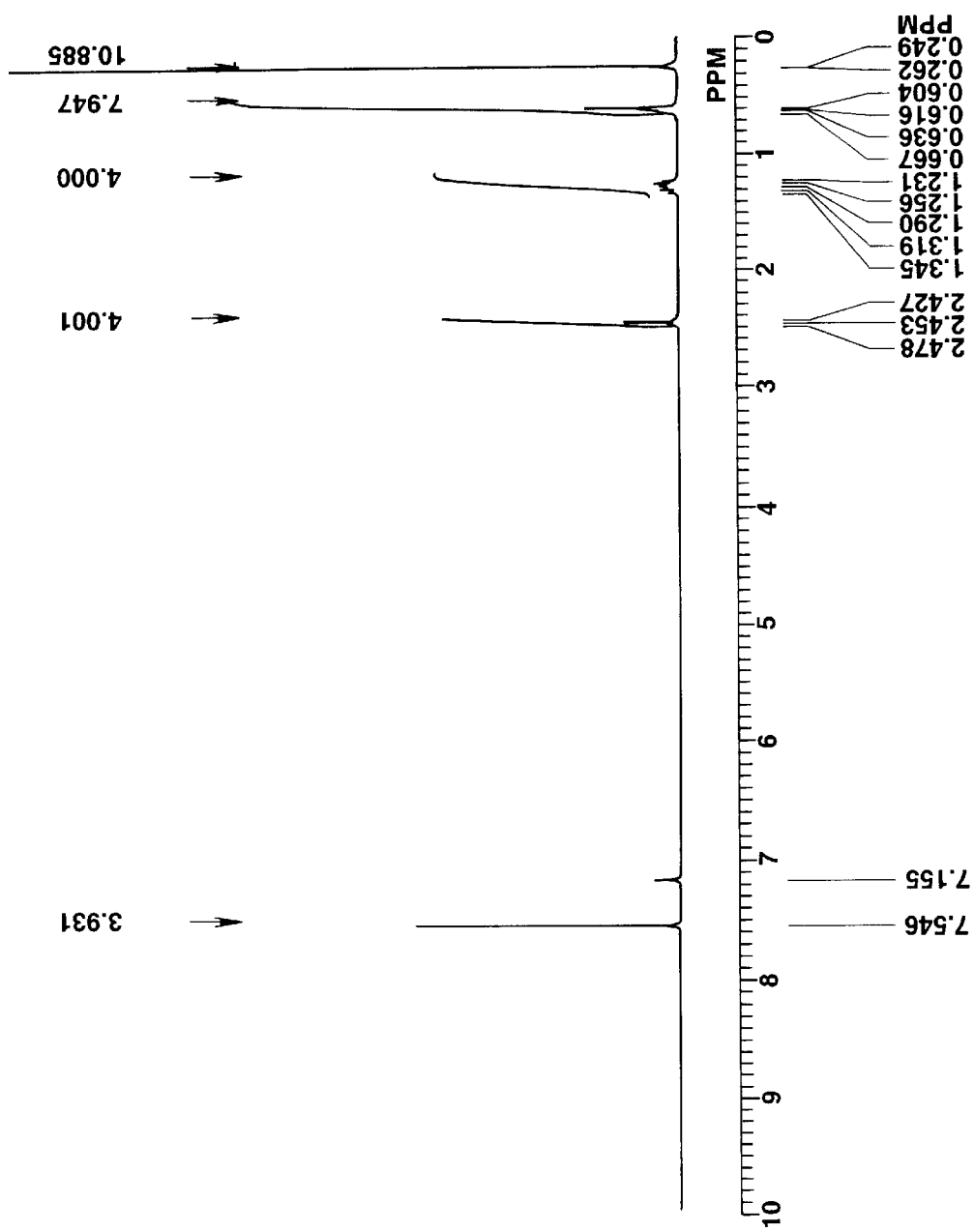
FIG. 1 is an NMR spectrum of the compound obtained in Example 1.
Figure 2:
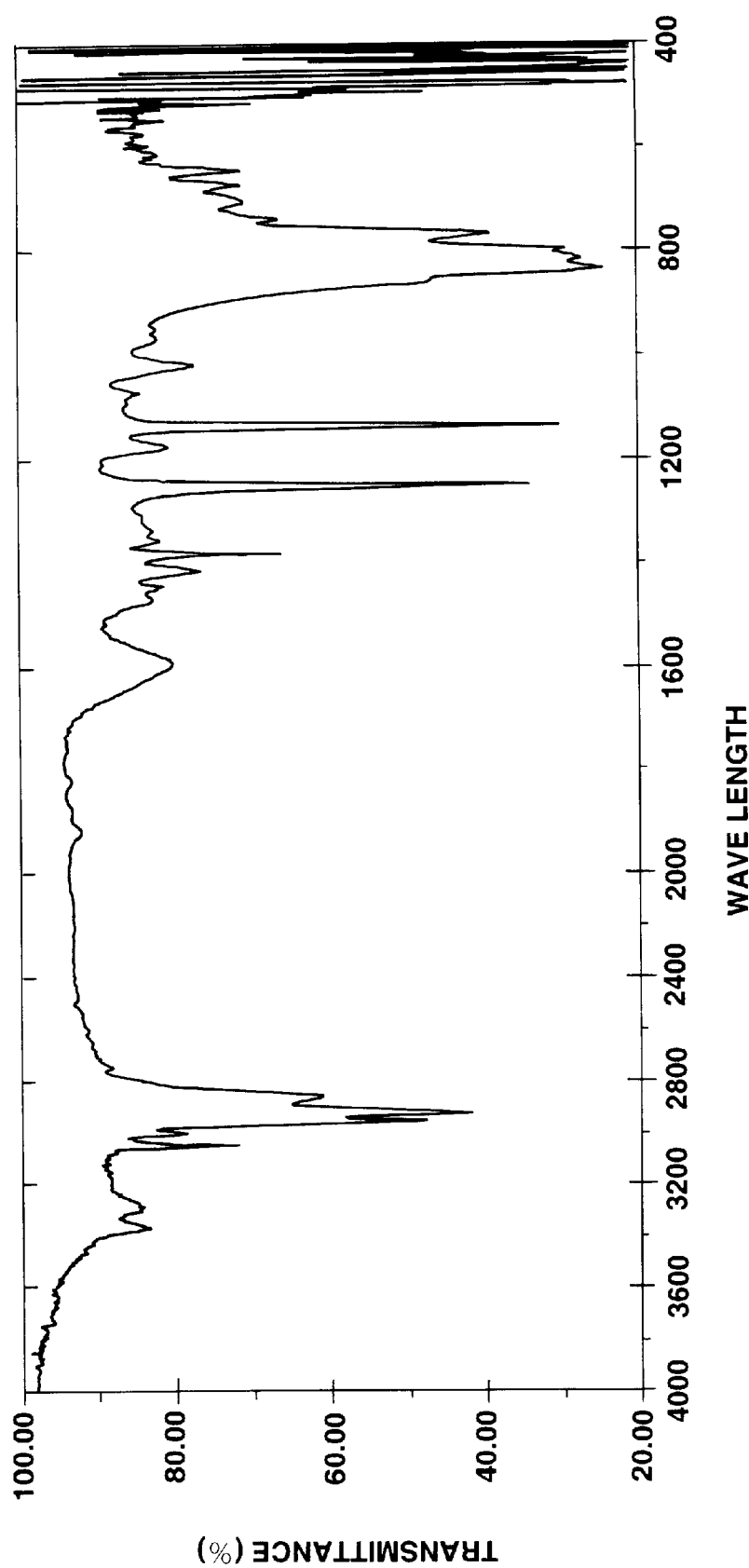
FIG. 2 is an IR spectrum of the compound obtained in Example 1.

The invention provides a process for preparing a bis(3-aminopropyldimethylsilyl)benzene compound of the following general formula (II), comprising the steps of effecting hydrosilylation reaction between N,N-bis(trimethylsilyl)allylamine and a bis(dimethylsilyl)benzene compound of the following general formula (I) in the presence of a platinum catalyst, followed by detrimethylsilylation (or trimethylsilyl-eliminating) reaction. The reaction scheme is shown below.

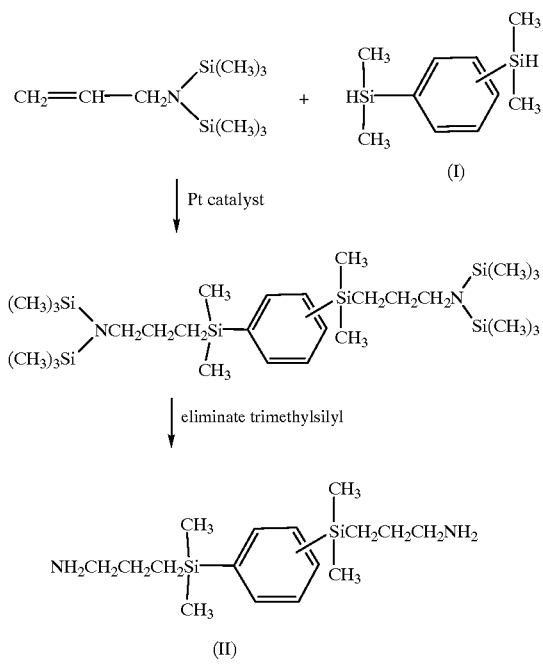

Illustrative of the bis(dimethylsilyl)benzene compound of the following general formula (I) are 1,2-bis(dimethylsilyl)benzene, 1,3-bis(dimethylsilyl)benzene, and 1,4-bis(dimethylsilyl)benzene.

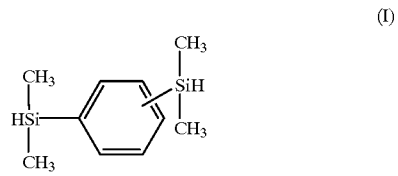

The hydrosilylation reaction between N,N-bis(trimethylsilyl)allylamine and a bis(dimethylsilyl)benzene compound is preferably carried out at 0 to 200° C., especially 40 to 120° C. These reactants are used in such amounts that 1 to 3 mol, especially 2 to 2.5 mol of N,N-bis(trimethylsilyl)allylamine is present per mol of the bis(dimethylsilyl)benzene compound. The reaction procedure, which is not critical, may be by adding N,N-bis (trimethylsilyl)allylamine to the bis(dimethylsilyl)-benzene compound or vice versa.

It is noted that as compared with N-(trimethylsilyl)-allylamine, N,N-bis(trimethylsilyl)allylamine is highly stable, least prone to hydrolysis with humidity in air and thus very easy to handle. For example, N,N-bis-(trimethylsilyl)allylamine can be commercially prepared by reacting allylamine with hexamethyldisilazane in the presence of a catalyst such as an arylsulfonic acid or salt thereof (as disclosed in Japanese Patent Application No. 37191/1997).

The platinum catalysts which can be used in the hydrosilylation reaction between N,N-bis(trimethylsilyl)-allylamine and bis(dimethylsilyl)benzene compound include metallic platinum, platinum compounds such as chloroplatinic acid, and platinum complexes having olefins or siloxane derivatives thereof as a ligand, such as [PtCl$_2$(PPh$_3$)$_2$] and platinum 1,3-divinyltetramethyl-disiloxane. An appropriate amount of the platinum catalyst used is 0.1 to 1,000 ppm, especially 10 to 200 ppm based on the reactant, N,N-bis(trimethylsilyl)-allylamine.

The reaction to eliminate trimethylsilyl may be readily carried out by mixing the reaction product of the above step with a compound having active hydrogen such as water or alcohols (e.g., methanol and ethanol). An appropriate amount of the compound having active hydrogen used is 1 to 100 mol per mol of the N,N-bis(trimethylsilyl)allylamine. Reaction is preferably carried out at 0 to 200° C., especially under reflux. No catalyst is necessary in this reaction with alcohols. For reducing the reaction time, catalysts including salts such as ammonium salts and acids such as p-toluenesulfonic acid may be added.

Both hydrosilylation and detrimethylsilylation reactions can be carried out in an essentially solventless system although aprotic solvents such as toluene, xylene, hexane, decane, and tetrahydrofuran may be used if desired.

Illustrative of the bis(3-aminopropyldimethylsilyl)-benzene compound of formula (II) produced by the process of the invention are 1,2-bis(3-aminopropyldimethylsilyl)-benzene, 1,3-bis(3-aminopropyldimethylsilyl)benzene, and 1,4-bis(3-aminopropyldimethylsilyl)benzene.

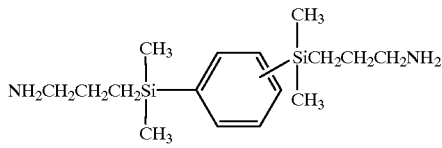

(II)

EXAMPLE

Examples of the invention are given below by way of illustration and not by way of limitation.

Synthetic Example 1

A 2-liter flask equipped with a stirrer, reflux condenser, thermometer and dropping funnel was charged with 48.6 g (2.0 mol) of metallic magnesium, 600 ml of tetrahydrofuran, and a small amount of iodine. To the flask kept at 50 to 60° C. in a nitrogen gas atmosphere, 235.9 g (1.0 mol) of p-dibromobenzene in 400 ml of tetrahydrofuran was added over 3 hours from the dropping funnel. The contents were stirred for 5 hours under reflux.

To the resulting Grignard reagent under water cooling, 189.2 g (2.0 mol) of dimethylchlorosilane was added dropwise over 2 hours from the dropping funnel. The contents were stirred for 3 hours under reflux. To this reaction solution was added 400 g of water. By liquid separating operation, the upper or organic layer was separated, from which a fraction of 73 to 75° C. at 6 mmHg was collected by distillation, yielding 140.0 g of 1,4-bis(dimethylsilyl)benzene.

Synthetic Example 2

A 2-liter flask equipped with a stirrer, reflux condenser, thermometer and dropping funnel was charged with 48.6 g (2.0 mol) of metallic magnesium, 600 ml of tetrahydrofuran, and a small amount of iodine. To the flask kept at 50 to 60° C. in a nitrogen gas atmosphere, 235.9 g (1.0 mol) of m-dibromobenzene in 400 ml of tetrahydrofuran was added over 3 hours from the dropping funnel. The contents were stirred for 5 hours under reflux.

To the resulting Grignard reagent under water cooling, 189.2 g (2.0 mol) of dimethylsilane was added dropwise over 2 hours from the dropping funnel. The contents were stirred for 3 hours under reflux. To this reaction solution was added 400 g of water. By liquid separating operation, the upper or organic layer was separated, from which a fraction of 86 to 87° C. at 10 mmHg was collected by distillation, yielding 112.8 g of 1,3-bis(dimethylsilyl)benzene.

Synthetic Example 3

A 500-ml flask equipped with a distillation column, stirrer, thermometer and dropping funnel was charged with 193.7 g (1.2 mol) of hexamethyldisilazane and 7.0 g (0.02 mol) of dodecylbenzenesulfonic acid. To the flask kept at 70° C., 114.2 g (2.0 mol) of allylamine was added over one hour from the dropping funnel. The contents were stirred for 3 hours under reflux. Subsequently, the allylamine was distilled off over 8 hours. From the reaction solution, a fraction of 89 to 90° C. at 40 mmHg was collected by vacuum distillation, yielding 192.0 g of N,N-bis(trimethylsilyl)allylamine.

Example 1

A 1-liter glass flask equipped with a stirrer, reflux condenser, thermometer and dropping funnel was charged with 201.5 g (1.0 mol) of N,N-bis(trimethylsilyl)-allylamine and 0.33 g of a 3% xylene solution of platinum 1,3-divinyltetramethyldisiloxane complex. To the flask kept at 60 to 65° C., 97.2 g (0.5 mol) of 1,4-bis-(dimethylsilyl)benzene was added dropwise over 3 hours from the dropping funnel. The reaction solution was allowed to ripen for 2 hours. 192.0 g (6.0 mol) of methanol was added to the reaction solution, which was kept under reflux for reaction for 6 hours. From the reaction solution, a fraction of 163 to 165° C. at 1 mmHg was collected in a yield of 142.0 g by vacuum distillation.

By mass spectroscopy (MS), nuclear magnetic resonance spectroscopy (NMR), and infrared absorption spectroscopy (IR), the compound thus obtained was identified to be 1,4-bis(3-aminopropyldimethylsilyl)benzene (yield 92%). Also, by gas chromatography, the compound was found to be free of isomers.

MS: m/z (attribution) 308 (molecular ion (M$^+$) peak) 293 (M$^+$-CH$_3$ ion peak) 116 (Si(CH$_3$)$_2$(CH$_2$CH$_2$CH$_2$NH$_2$) ion peak)

NMR: FIG. 1 (solvent: C$_6$D$_6$)

IR: FIG. 2

Comparative Example 1

A reaction solution was obtained by the same procedure as in Example 1 except that 129.3 g (1.0 mol) of N-(trimethylsilyl)allylamine was used instead of 201.5 g (1.0 mol) of N,N-bis(trimethylsilyl)allylamine. On gas chromatographic analysis, the reaction solution was found to contain 9.0% of a by-product as a compound having an approximate boiling point to the end (3-aminopropyl-dimethylsilyl)benzene. On mass spectroscopic analysis, the by-product was found to be an isomer.

Example 2

A 1-liter glass flask equipped with a stirrer, reflux condenser, thermometer and dropping funnel was charged with 201.5 g (1.0 mol) of N,N-bis(trimethylsilyl)-allylamine and 0.33 g of a 3% xylene solution of platinum 1,3-divinyltetramethyldisiloxane complex. To the flask kept at 60 to 65° C., 97.2 g (0.5 mol) of 1,3-bis-(dimethylsilyl) benzene was added dropwise over 3 hours from the dropping funnel. The reaction solution was allowed to ripen for 2 hours. 192.0 g (6.0 mol) of methanol was added to the reaction solution, which was kept under reflux for reaction for 6 hours. From the reaction solution, a fraction of 154 to 155° C. at 0.35 mmHg was collected in a yield of 125.0 g by vacuum distillation.

By mass spectroscopy (MS), nuclear magnetic resonance spectroscopy (NMR), and infrared absorption spectroscopy (IR), the compound thus obtained was identified to be 1,3-bis(3-aminopropyldimethylsilyl)benzene (yield 81%). Also, by gas chromatography, the compound was found to be free of isomers.

MS: m/z (attribution) 308 (molecular ion (M$^+$) peak) 293 (M$^+$-CH$_3$ ion peak) 116 (Si(CH$_3$)$_2$(CH$_2$CH$_2$CH$_2$NH$_2$) ion peak)

Figure 3:
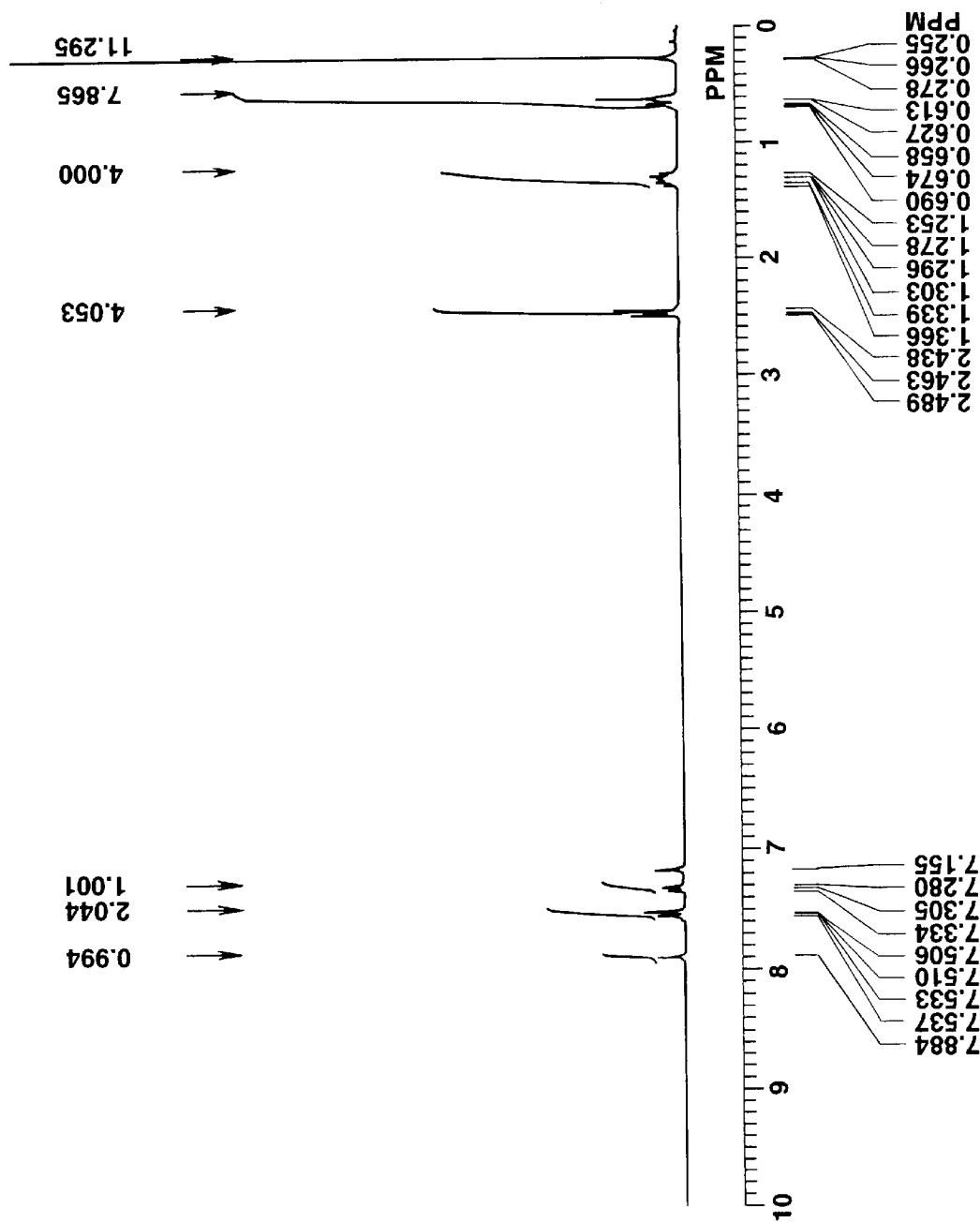
FIG. 3 is an NMR spectrum of the compound obtained in Example 2.
Figure 4:
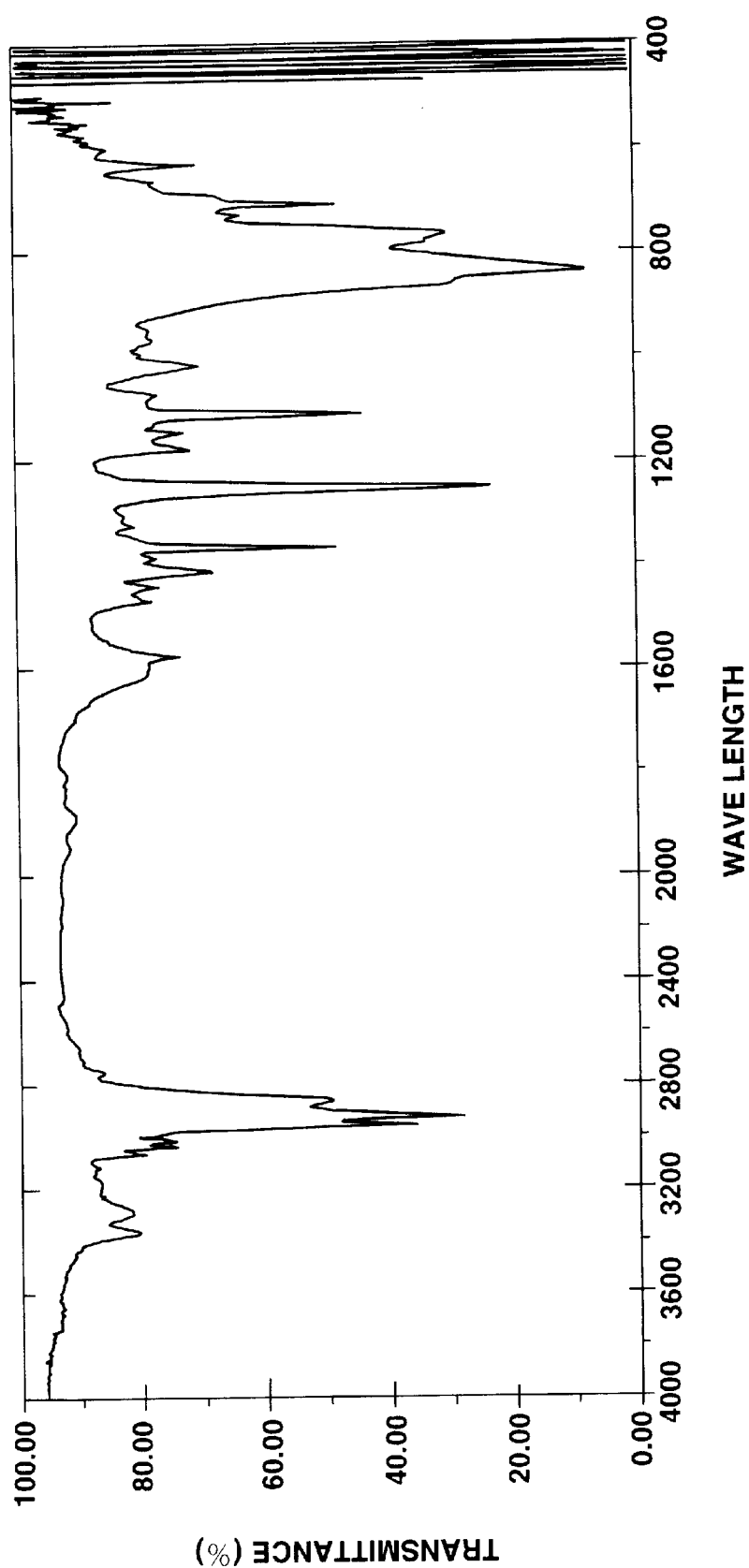
FIG. 4 is an IR spectrum of the compound obtained in Example 2.

NMR: FIG. 3 (solvent: C$_6$D$_6$)

IR: FIG. 4

There has been described a simple and inexpensive process for preparing a bis(3-aminopropyldimethylsilyl)-benzene compound in high yields without forming isomers.

Japanese Patent Application No. 145079/1998 is incorporated herein by reference.

Reasonable modifications and variations are possible from the foregoing disclosure without departing from either the spirit or scope of the present invention as defined by the claims.

What is claimed is:

1. A process for preparing a bis(3-aminopropyl-dimethylsilyl)benzene compound, comprising the steps of effecting hydrosilylation reaction between N,N-bis (trimethylsilyl)allylamine and a bis(dimethylsilyl)-benzene compound of the following general formula (I):

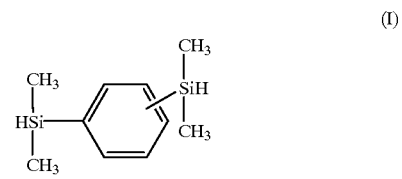

in the presence of a platinum catalyst, and effecting detrimethylsilylation reaction to form a bis(3-amino-propyldimethylsilyl)benzene compound of the following general formula (II):

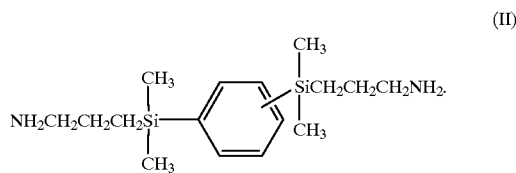

.

* * * * *